United States Patent
Metten et al.

(10) Patent No.: US 9,681,724 B2
(45) Date of Patent: Jun. 20, 2017

(54) METHOD FOR THE GENTLE HEAT-ASSISTED SHAPING OF KERATIN FIBERS

(71) Applicant: CRODA INTERNATIONAL, PLC., East Yorkshire (GB)

(72) Inventors: Diane Metten, Hamburg (DE); Bernd Richters, Hamburg (DE); Rene Scheffler, Ellerau (DE)

(73) Assignee: CRODA INTERNATIONAL PLC, East Yorkshire (GB)

( * ) Notice: Subject to any disclaimer, the term of this patent is extended or adjusted under 35 U.S.C. 154(b) by 0 days.

(21) Appl. No.: 14/742,791

(22) Filed: Jun. 18, 2015

(65) Prior Publication Data

US 2015/0282582 A1 Oct. 8, 2015

Related U.S. Application Data

(63) Continuation of application No. PCT/EP2013/073472, filed on Nov. 11, 2013.

(30) Foreign Application Priority Data

Dec. 21, 2012 (DE) ........................ 10 2012 224 143

(51) Int. Cl.
    *A61Q 5/06* (2006.01)
    *A45D 7/06* (2006.01)
    *A61K 8/49* (2006.01)

(52) U.S. Cl.
    CPC .............. *A45D 7/06* (2013.01); *A61K 8/4946* (2013.01); *A61Q 5/06* (2013.01)

(58) Field of Classification Search
    None
    See application file for complete search history.

(56) References Cited

U.S. PATENT DOCUMENTS

| 2,647,125 | A | 7/1953 | Gunderson |
| 6,787,128 | B2 | 9/2004 | Kleen et al. |
| 8,784,785 | B2 | 7/2014 | Hentrich et al. |
| 9,005,593 | B2 * | 4/2015 | Dutheil-Gouret ...... A61K 8/731 424/70.12 |

FOREIGN PATENT DOCUMENTS

| DE | 102008031700 A1 | 1/2010 |
| JP | 2010-189309 A | 9/2010 |
| WO | 87/06826 A1 | 11/1987 |
| WO | 98/51265 A1 | 11/1998 |

OTHER PUBLICATIONS

Formulation Guide, Personal Care, Step Communications, Tunbridge Wells, GB , Apr. 2012, pp. 148-149, XP007922939, ISSN: 1470-8213, Retrieved from the Internet: URL: http://content.yudu.com/A1whtp/PCapril12/resources/149.htm.*
PCT International Search Report (PCT/EP2013/073472) dated Dec. 11, 2014.
McMullen et al., "Thermal Degradation of Hair. I. Effect of Curling Irons", Journal of Cosmetic Science, vol. 49, pp. 223-244, 1998.
Database GNPD [Online] Mintel, "Heat Protection Styling Spray", XP002732406, Database accession No. 10255740, Mar. 2006.

* cited by examiner

*Primary Examiner* — Jyothsna Venkat
(74) *Attorney, Agent, or Firm* — Ratnerprestia

(57) ABSTRACT

A compound of formula (I) in which R1, R2 and R3 independently represent an aliphatic hydrocarbon group with 6 to 30 carbon atoms, and n and m independently represent integers from 1 to 10, is suitable for restructuring keratin-containing fibers that were exposed to heat of a temperature of 80° C. to 350° C.

18 Claims, No Drawings

METHOD FOR THE GENTLE HEAT-ASSISTED SHAPING OF KERATIN FIBERS

FIELD OF THE INVENTION

The present invention generally relates to the technical field of styling keratin-containing fibers.

BACKGROUND OF THE INVENTION

In principle, all animal hair, such as wool, horsehair, angora wool, furs, feathers, and products or textiles produced therefrom, can be used as keratin-containing fibers. However, the invention is preferably used within the scope of heat-assisted hair shaping, in particular straightening of curly human hair and wigs produced therefrom.

A reshaping of keratin-containing fibers is usually carried out in such a way that the fiber is mechanically reshaped and the reshaped form is fixed using appropriate aids. Prior to and/or after this reshaping, the fiber is treated with at least one cosmetic preparation so as to fix the shape that has been newly impressed on the collective fibers.

Within the scope of a permanent wave, for example, keratin-containing fibers are treated with keratin-reducing compounds. After a rinsing process, the fiber is then treated in what is known as the fixation step with an oxidizing agent preparation, rinsed, and freed of the reshaping aids (such as rollers, curlpapers) after or during the fixation step. When a thiol, such as ammonium thioglycolate, is used as the keratin-reducing component, it breaks some of the disulfide bonds of the keratin molecule into —SH groups, whereby the keratin fibers are softened. During the later oxidative fixation, disulfide bonds are again formed in the hair keratin, so that the keratin structure is fixed in the predefined reshaped form.

Within the scope of a temporary styling process, the newly impressed shape of the collective fibers is fixed by applying what are known as hair fixatives. Such hair fixatives are waxes or setting polymers, for example.

When hydrous cosmetics are used, the moist keratin-containing fibers are frequently shaped, the shape is initially mechanically fixed, so as to then remove the water by the application of heat, and additionally bring about fixation of the new shape by the re-formation of the hydrogen bonds within and between the keratin protein strands.

So as to straighten keratin-containing fibers, the curly hair is either wrapped onto rollers having a large diameter of typically more than 15 mm, or the hair is combed straight under the action of a keratin-reducing composition, for example, in a corresponding method.

Instead of using rollers, it is also possible to straighten the fiber on a straightening board. Straightening boards are usually rectangular panels made of plastic material, for example. The fiber is preferably wetted with a liquid. The fibers which are mechanically fixed in the new shape are subjected to a heat treatment as a supporting measure, for example by a hot blower or contact with hot surfaces.

One option of straightening hair is to straighten it with a hot iron. However, the structure of the keratin-containing fiber changes during straightening when heat-treating the hair (see in this regard R. McMullen et al., J. Cosmet. Sci., 1998, 49, 223-244). This change in the fiber structure should be counteracted by appropriate measures or repaired thereafter.

BRIEF SUMMARY OF THE INVENTION

Use of at least one compound of formula (I)

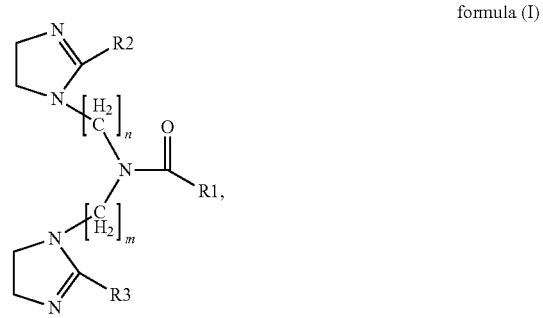

formula (I)

where R1, R2 and R3 independently of each other denote an aliphatic hydrocarbon group having 6 to 30 carbon atoms; and n and m independently of each other denote integers from 1 to 10, for restructuring keratin-containing fibers which were exposed to heat having a temperature of 80° C. to 350° C. (preferably 80° C. to 280° C., particularly preferably 100° C. to 250° C., and more preferably 140° C. to 220° C.).

Method for shaping, more particularly for straightening, keratin-containing fibers, in particular human hair, wherein (i) the fibers are subjected to a heat treatment; (ii) the heat-treated fibers, subsequently to the heat treatment, are post-treated with a cosmetic agent which includes at least one compound of formula (I) in a cosmetic carrier

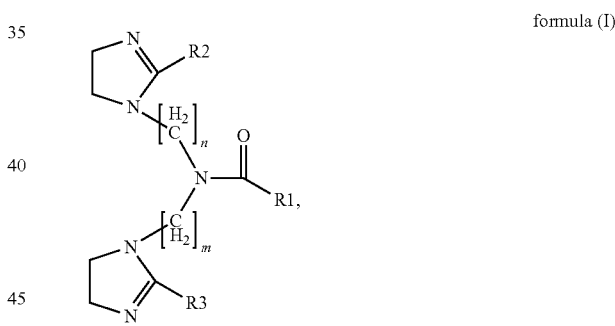

formula (I)

where R1, R2 and R3 independently of each other denote an aliphatic hydrocarbon group having 6 to 30 carbon atoms; and n and m independently of each other denote integers from 1 to 10; (iii) and the fibers are reshaped after, prior to or during step (i) by way of reshaping aids.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It is the object of the invention to provide a heat-assisted shaping method for keratin-containing fibers, in particular for human hair, which provides very good shape fixation, conditions the fiber, and is gentle on or repairs the structure of the fiber.

Surprisingly it was found that the object is achieved by a shaping method for keratin-containing fibers, in particular human hair, which provides for a post-treatment step using a special cosmetic active agent after the application of heat.

Furthermore, other desirable features and characteristics of the present invention will become apparent from the subsequent detailed description of the invention and the appended claims, taken in conjunction with the accompanying drawings and this background of the invention.

A first subject matter of the invention is the use of at least one compound of formula (I)

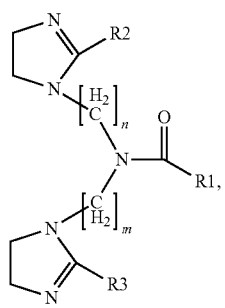

formula (I)

where

R1, R2 and R3 independently of each other denote an aliphatic hydrocarbon group having 6 to 30 carbon atoms; and n and m independently of each other denote integers from 1 to 10, for restructuring keratin-containing fibers which were exposed to heat having a temperature of 80° C. to 350° C. (preferably 80° C. to 280° C., particularly preferably 100° C. to 250° C., and more preferably 140° C. to 220° C.). Preferably a hot air blower (for example, in the form of a blow dryer, hood dryer, curling rod), a straightening iron or a hair curler is used as the heat source. Straightening irons or hair curlers are particularly preferred heat sources.

Said aliphatic hydrocarbon group of the groups R1, R2 and R3 according to above formula (I) can be linear or branched.

Said aliphatic hydrocarbon groups of the groups R1, R2 and R3 according to above formula (I) preferably denotes a C6 to C30 alkyl group or a C6 to C30 alkenyl group (particularly preferably a C8 to C24 alkyl group or a C8 to C24 alkenyl group, especially particularly preferably a C10 to C20 alkyl group or a C10 to C20 alkenyl group, and most preferably a C12 to C18 alkyl group or a C12 to C18 alkenyl group).

It is preferred according to the invention for at least the groups R2 and R3 of the formula (I) to be identical. Most preferably all groups R1 and R2 and R3 are identical (R1 identical to R2 identical to R3).

It is preferred according to the invention if according to formula (I) n=m.

It is preferred according to the invention if according to above formula (I) n and m denote integers from 2 to 6, and most preferably 2, 3 and/or 4, wherein again preferably n=m.

According to above formula (I), R1 to R3 preferably denote capryl, caprylyl, octyl, nonyl, decanyl, lauryl, myristyl, cetyl, stearyl, isostearyl, oleyl, behenyl or arachidyl. Moreover, it again particularly preferably applies that R2 is identical to R3, and most preferably that R1 is identical to R2 is identical to R3. The letters n and m independently of each other denote integers from 1 to 10, preferably from 2 to 6, and most preferably 2, 3 and/or 4, wherein most preferably n=m.

According to above formula (I), most preferably R1 is identical to R2 is identical to R3, and they are selected from capryl, caprylyl, octyl, nonyl, decanyl, lauryl, myristyl, cetyl, stearyl, isostearyl, oleyl, behenyl or arachidyl, and n=m=2. Most preferably R1=R2=R3, and they are selected from lauryl, myristyl, cetyl, stearyl, isostearyl, oleyl, behenyl or arachidyl, among which cetyl, stearyl, isostearyl, oleyl or behenyl are particularly preferred and n=m=2.

The most preferred compound of formula (I) is that which bears the INCI name Bis-Ethyl(isostearylimidazoline) Isostearamide. The latter compound is commercially available from Croda under the trade name Keradyn® HH.

Especially particularly preferably, said compound of above formula (I) is used within the scope of a restructuring process of keratin-containing fibers, in particular human hair, previously subjected to a heat-assisted straightening process at a temperature of 80° C. to 350° C. (preferably 80° C. to 280° C., particularly preferably 100° C. to 250° C., more preferably 140° C. to 220° C.).

Within the scope of the use according to the invention, it has been found to be favorable, and thus preferred according to the invention, to incorporate at least one compound of above formula (I) into a cosmetic carrier, and to use the resulting cosmetic agent to post-treat the fibers within the scope of a heat-assisted shaping process.

The agents used according to the invention preferably include the compounds of above formula (I) in an amount of 0.01 to 15.0 wt. %, particularly preferably of 0.1 to 10.0 wt. %, especially particularly preferably of 0.1 to 7.5 wt. %, and most preferably of 0.3 to 5.0 wt. %, in each case based on the weight of the ready-to-use agent.

Within the scope of one embodiment of the invention, it is preferred for the agent used according to the invention to additionally include at least one setting polymer, selected from at least one compound of the group consisting of setting nonionic polymers, setting anionic polymers, setting amphoteric polymers and setting cationic polymers.

In addition, the agent used according to the invention preferably includes at least one setting cationic polymer. The additional setting cationic polymers comprise at least one structural unit that includes at least one permanently cationized nitrogen atom. Permanently cationized nitrogen atoms shall be understood to mean such nitrogen atoms which carry a positive charge and thereby form a quarternary ammonium compound. Quaternary ammonium compounds are generally produced by reacting tertiary amines with alkylating agents, such as methyl chloride, benzyl chloride, dimethyl sulfate or dodecyl bromide, but also ethylene oxide. Depending on the tertiary amine that is used, in particular the following groups are known: alkyl ammonium compounds, alkenyl ammonium compounds, imidazolinium compounds, and pyridinium compounds.

Within the meaning of this embodiment, preferred agents include the setting cationic polymers in an amount of 0.1 wt. % to 20.0 wt. %, particularly preferably of 0.2 wt. % to 10.0 wt. %, and especially particularly preferably of 0.5 wt. % to 5.0 wt. %, in each case based on the weight of the agent.

According to the invention, the cationic setting polymers can be selected from cationic quaternized cellulose derivatives.

In general those cationic quaternized celluloses which carry more than one permanent cationic charge in a side chain have proven to be advantageous within the meaning of the embodiment. Among the cationic cellulose derivatives, those that are produced by a reaction of hydroxyethyl cellulose with a diallyl dimethyl ammonium reactant (in particular diallyl dimethyl ammonium chloride), optionally in the presence of further reactants, shall be particularly emphasized. Among these cationic celluloses, in turn, those cationic celluloses having the INCI designation Polyquaternium-4 are particularly suitable.

Also suitable are those cationic setting polymers which comprise at least one structural unit of formula (N1) and at least one structural unit of formula (N2), and optionally at least one structural unit of formula (K1)

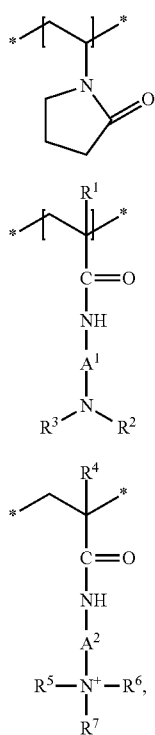

where
$R^1$ and $R^4$ independently of each other denote a hydrogen atom or a methyl group;
$A^1$ and $A^2$ independently of each other denote an ethane-1,2-diyl, propane-1,3-diyl or butane-1,4-diyl group;
$R^2$, $R^3$, $R^5$ and $R^6$ independently of each other denote a ($C_1$ to $C_4$) alkyl group; and
$R^7$ denotes a ($C_8$ to $C_{30}$) alkyl group.

Suitable compounds are, for example:
copolymers of dimethylaminoethyl methacrylate, quaternized with diethyl sulfate, with N-vinylpyrrolidone with the INCI designation Polyquaternium-11;
copolymers of methacryloylaminopropyl lauryldimethylammonium chloride with N-vinylpyrrolidone and dimethylaminopropyl methacrylamide with the INCI designation Polyquaternium-55;
copolymers of methacryloylaminopropyl lauryldimethylammonium chloride with N-vinylpyrrolidone and N-vinylcaprolactam and dimethylaminopropyl methacrylamide with the INCI designation Polyquaternium-69.

Setting cationic polymers usable particularly preferably within the meaning of the embodiment are also those setting cationic copolymers which include a copolymer (c1) which, in addition to at least one structural element of formula (K2), additionally comprises a structural element of formula (N1)

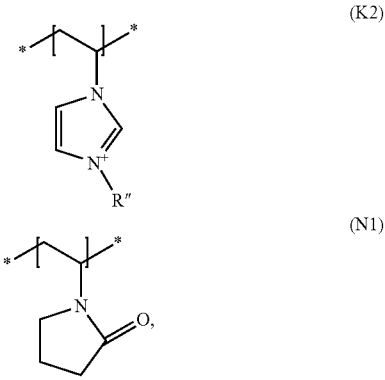

where
R″ denotes a ($C_1$ to $C_4$) alkyl group, in particular a methyl group.

Particularly preferred N-methylvinylimidazol/vinylpyrrolidone copolymers are referred to as Polyquaternium-16 according to INCI nomenclature. The preferred N-methylvinylimidazol/vinylpyrrolidone copolymers are referred to as Polyquaternium-44 according to INCI nomenclature.

Also preferred are N-methylvinylimidazol/vinylpyrrolidone/vinylcaprolactam copolymers, which are referred to as Polyquaternium-46 according to INCI nomenclature.

Additionally preferred are N-methylvinylimidazol/vinylpyrrolidone/vinylimidazol/methacrylamide copolymers, which are referred to as Polyquaternium-68 according to INCI nomenclature.

Especially particularly preferred copolymers (c3) include 1 to 12 mol %, preferably 3 to 9 mol %, and particularly 6 mol % structural units according to formula (K2-a), and 45 to 65 mol %, preferably 50 to 60 mol %, and particularly 55 mol % structural units according to formula (N1), and 1 to 20 mol %, preferably 5 to 15 mol %, and particularly 10 mol % structural units according to formula (N3), and 20 to 40 mol %, preferably 25 to 35 mol %, and particularly 29 mol % structural units according to formula (N4).

Among the additional setting cationic polymers selected from the cationic polymers having at least one structural element of above formula (K2), the following are considered to be preferred:
N-vinylpyrrolidone/1-vinyl-3-methyl-1H-imidazolium chloride copolymers;
N-vinylpyrrolidone/1-vinyl-3-methyl-1H-imidazolium methyl sulfate copolymers;
N-vinylpyrrolidone/N-vinylcaprolactam/1-vinyl-3-methyl-1H-imidazolium terpolymer;
N-vinylpyrrolidone/methacrylamide/N-vinylimidazol/1-vinyl-3-methyl-1H-imidazolium methyl sulfate copolymer;
and mixtures of these polymers.

The agent according to the invention preferably includes at least one setting nonionic polymer as an additional setting polymer. According to the invention, a nonionic polymer is understood to mean a polymer that, in a protic solvent under standard conditions, essentially does not carry any structural units having permanently cationic or anionic groups which must be compensated for with counterions, preserving electroneutrality. The setting nonionic polymers are preferably present in the agent of this embodiment according to the invention in an amount of 0.1 wt. % to 20.0 wt. %, particularly preferably of 0.2 wt. % to 15.0 wt. %, and especially particularly preferably of 0.5 wt % to 10.0 wt. %, in each case based on the weight of the agent according to the invention.

The agents according to the invention particularly preferably include at least one chitosan as the nonionic setting polymer. In addition to the chitosans as typical biopolymers, alkoxylated chitosans may be used as derivatives within the meaning of the invention. Agents that are preferred according to the invention are characterized in that the chitosan they include is at least one neutralization product of chitosan having at least one organic carboxylic acid. It is preferred according to the invention to select the organic carboxylic acid from lactic acid, pyrrolidone carboxylic acid, nicotinic acid, hydroxyisobutyric acid, hydroxyisovaleric acid or mixtures of these acids. The chitosans or the derivatives thereof are preferably present in the agents according to the invention in an amount of 0.01 wt. % to 5 wt. %, particularly preferably of 0.05 wt. % to 2.0 wt. %, and especially particularly preferably of 0.1 wt. % to 1 wt. %, in each case based on the weight of the agent according to the invention.

The setting nonionic polymers are preferably selected from at least one polymer of the group consisting of
homopolymers and nonionic copolymers of N-vinylpyrrolidone,
homopolymers and nonionic copolymers of vinyl alcohol,
nonionic copolymers of isobutene.

Agents that, as the setting nonionic polymer, include at least one polymer selected from the group consisting of
polyvinylpyrrolidone,
copolymers of N-vinylpyrrolidone and vinyl esters of carboxylic acids having 2 to 18 carbon atoms, in particular of N-vinylpyrrolidone and vinyl acetate,
copolymers of N-vinylpyrrolidone and N-vinylimidazol and methacrylamide,
copolymers of N-vinylpyrrolidone and N-vinylimidazol and acrylamide,
copolymers of N-vinylpyrrolidone with N,N-di($C_1$ to $C_4$)-alkylamino-($C_2$ to $C_4$)-alkyl acrylamide
are especially particularly preferred according to the invention.

Agents that, as the setting nonionic polymer, include at least one polymer selected from the group consisting of V-vinylpyrrolidone and vinyl acetate, are most preferred according to the invention.

The agents according to the invention can also include at least one setting amphoteric polymer as the setting polymer. One example of a setting amphoteric polymer that can be used according to the invention is the acrylic resin available by the designation Amphomer®, which is a copolymer of tert-butylaminoethyl methacrylate, N-(1,1,3,3-tetramethylbutyl)acrylamide, and two or more monomers from the group consisting of acrylic acid, methacrylic acid, and the simple alkyl esters thereof. The setting amphoteric polymers are preferably present in the water-based compositions that can be used according to the invention in amounts of 0.01 wt. % to 20 wt. %, and particularly preferably of 0.05 to 10 wt. %, based on the total agent. Amounts of 0.1 to 5 wt. % are especially particularly preferred.

Moreover, at least one setting anionic polymer can be used as setting polymers. If the agent according to the invention includes a setting anionic polymer, it is preferably present in the form of a spray, and more particularly an aerosol spray. The setting anionic polymers are preferably present in the agent according to the invention in an amount of 0.1 wt. % to 20.0 wt. %, particularly preferably of 0.2 wt. % to 15.0 wt. %, and especially particularly preferably of 0.5 wt. % to 10.0 wt. %, in each case based on the total agent.

Particularly preferred polymers of this type are selected from at least one polymer of the group consisting of
copolymers of vinyl acetate and crotonic acid,
copolymers of vinyl propionate and crotonic acid,
copolymers of vinyl neodecanoate, vinyl acetate and crotonic acid.

Particularly preferred polymers are selected from at least one polymer of the group consisting of copolymers of acrylic acid and ethyl acrylate and N-tert-butylacrylamide. Moreover, the water-based composition that can be used according to the invention can include at least one polyurethane having at least one carboxyl group (for example, a copolymer of isophthalic acid, adipic acid, 1,6-hexanediol, and neopentylglycol) as the anionic setting polymer. The setting anionic polymers are preferably present in an amount of 0.1 wt. % to 15 wt. %, and more particularly of 0.5 wt. % to 10 wt. %, in each case based on the weight of the water-based composition.

It has been found to be particularly preferred for the agents according to the invention to additionally include at least one cationic surfactant. Cationic surfactants, in turn, are selected from quarternary ammonium compounds, esterquats and amidoamines, or mixtures thereof. Preferred quaternary ammonium compounds are ammonium halides, in particular chlorides and bromides, such as alkyl trimethylammonium chlorides, dialkyldimethylammonium chlorides and trialkylmethylammonium chlorides, such as cetyl trimethylammonium chloride, stearyl trimethylammonium chloride, distearyl dimethylammonium chloride, lauryl dimethylammonium chloride, lauryl dimethyl benzylammonium chloride and tricetyl methylammonium chloride, and the imidazolium compounds known under the INCI designations Quaternium-27 and Quaternium-83. The long alkyl chains of the above-mentioned surfactants preferably comprise 10 to 18 carbon atoms.

Esterquats are known substances, which both comprise at least one ester function and at least one quaternary ammonium group as structural element. Preferred esterquats are quaternized ester salts of fatty acids with triethanolamine, quaternized ester salts of fatty acids with diethanol alkylamines, and quaternized ester salts of fatty acids with 1,2-dihydroxypropyl dialkylamines.

The alkylamidoamines are usually produced by the amidation of natural or synthetic fatty acids and fatty acid fractions with dialkylaminoamines. A particularly suitable compound according to the invention from this substance group is stearamidopropyl dimethylamine, commercially available under the designation Tegoamid® S 18.

The cationic surfactants are preferably present in the agents according to the invention in amounts of 0.05 to 10 wt. %, based on the total agent. Amounts of 0.1 to 5 wt. % are particularly preferred.

It has been found to be particularly preferred for the agents according to the invention to additionally include at least one nonionic surfactant.

Nonionic surfactants include a polyol group, a polyalkylene glycol ether group or a combination of a polyol and polyglycol ether group, for example, as the hydrophilic group. Such compounds are, for example:
addition products of 2 to 100 mole ethylene oxide and/or 1 to 5 mole propylene oxide to linear and branched fatty alcohols having 8 to 30 carbon atoms, to fatty acids having 8 to 30 carbon atoms, and to alkyl phenols having 8 to 15 carbon atoms in the alkyl group;

addition products, end group-capped with a methyl group or ($C_2$ to $C_6$)alkyl group, of 2 to 50 mole ethylene oxide and/or 1 to 5 mole propylene oxide to linear and branched fatty alcohols having 8 to 30 carbon atoms, to fatty acids having 8 to 30 carbon atoms, and to alkyl phenols having 8 to 15 carbon atoms in the alkyl group;

$C_{12}$-$C_{30}$ fatty acid monoesters and diesters of addition products of 1 to 30 mole ethylene oxide to glycerol;

addition products of 5 to 60 mole ethylene oxide to castor oil and hydrogenated castor oil;

polyol fatty acid esters;

alkoxylated triglycerides;

alkoxylated fatty acid alkyl esters of formula (E4-I)

$$R^1CO\text{—}(OCH_2CHR^2)_wOR^3 \quad (E4\text{-}I),$$

in which $R^1CO$ denotes a linear or branched, saturated and/or unsaturated acyl group having 6 to 22 carbon atoms, $R^2$ denotes hydrogen or methyl, $R^3$ denotes linear or branched alkyl groups having 1 to 4 carbon atoms, and w denotes numbers from 1 to 20;

amine oxides;

sorbitan fatty acid esters and addition products of ethylene oxide to sorbitan fatty acid esters, such as polysorbates;

sugar fatty acid esters and addition products of ethylene oxide to sugar fatty acid esters;

addition products of ethylene oxide to fatty acid alkanolamides and fatty amines;

sugar surfactants of the alkyl and alkenyl oligoglycoside type according to formula (E4-II)

$$R_4O\text{-}[G]p \quad (E4\text{-}II),$$

where $R^4$ denotes an alkyl or alkenyl group having 4 to 22 carbon atoms, G denotes a sugar group having 5 or 6 carbon atoms, and p denotes numbers from 1 to 10. They can be obtained according to the relevant methods of preparative organic chemistry.

Addition products of alkylene oxide to saturated linear fatty alcohols and fatty acids, each having 2 to 100 mole ethylene oxide per mole of fatty alcohol or fatty acid, have proven to be especially particularly preferred nonionic surfactants. Preparations having excellent properties are likewise obtained if they include $C_{12}$-$C_{30}$ fatty acid monoesters and diesters of addition products of 1 to 30 mole ethylene oxide to glycerol and/or addition products of 5 to 60 mole ethylene oxide to castor oil and hydrogenated castor oil as nonionic surfactants.

The agents according to the invention especially particularly preferably include at least one addition product of 15 to 100 mole ethylene oxide, and more particularly of 15 to 50 mole ethylene oxide, to a linear or branched (in particular linear) fatty alcohol having 8 to 22 carbon atoms as the surfactant. These are especially particularly preferably ceteareth-15, ceteareth-25 or ceteareth-50, which are marketed as Eumulgin® CS 15 (COGNIS), Cremophor A25 (BASF SE) or Eumulgin® CS 50 (COGNIS).

The agents used according to the invention can furthermore include auxiliary agents and additives, which are typically added to conventional styling agents.

In particular additional care substances should be mentioned as suitable auxiliary agents and additives.

A silicone oil and/or a silicone gum can be used as a care substance, for example.

Silicone oils or silicone gums suitable according to the invention are in particular dialkyl and alkyaryl siloxanes, such as dimethyl polysiloxane and methylphenyl polysiloxane, and the alkoxylated, quaternized or anionic derivatives thereof. Cyclic and linear polydialkylsiloxanes, the alkoxylated and/or aminated derivatives thereof, dihydroxy polydimethylsiloxanes and polyphenylalkylsiloxanes are preferred.

Dimethicones form the second group of silicones that can also be present according to the invention. These can be either linear or branched, or cyclic or cyclic and branched. Dimethicone copolyols form a further group of silicones that are suitable. Particularly suitable silicones are aminofunctional silicones, and more particularly silicones that are combined under the INCI designation Amodimethicone.

The agents preferably include the silicones in amounts of 0.01 wt. % to 15 wt. %, and particularly preferably of 0.05 to 2 wt. %, based on the total agent.

The agent can include at least one protein hydrolysate and/or one of the derivatives thereof, for example, as a care substance of another compound class. The protein hydrolysates are present in the agents according to the invention, for example, in concentrations of 0.1 wt. % to 20.0 wt. %, preferably of 0.05 wt. % to 15.0 wt. %, and especially particularly preferably in amounts of 0.5 wt. % to 5.0 wt. %, in each case based on the total application preparation.

The agent according to the invention can furthermore include at least one vitamin, provitamin, vitamin precursor and/or one of the derivatives thereof as a care substance. D-panthenol, optionally in combination with at least one of the above-mentioned silicone derivatives, is used especially particularly preferably as a care substance.

The agents according to the invention can furthermore include at least one plant extract as a care agent.

Monosaccharides or oligosaccharides can also be used as care substance in the agents according to the invention. The monosaccharides or oligosaccharides are preferably present in the agents according to the invention in an amount of 0.1 to 8 wt. %, and particularly preferable 1 to 5 wt. %, based on the total application preparation.

The agent can furthermore include at least one lipid as care substance. The agents according to the invention preferably include the lipids in amounts of 0.01 to 10 wt. %, and more particularly of 0.1 to 5 wt. %, based on the total application preparation.

Moreover, oleosomes are suitable as care substance.

Among the natural and synthetic cosmetic oleosomes are, for example:

vegetable oils;

liquid paraffin oils, isoparaffin oils and synthetic hydrocarbons, and di-n-alkyl ethers having in total between 12 and 36 carbon atoms, in particular 12 to 24 carbon atoms, such as di-n-octyl ether, di-n-decyl ether, di-n-nonyl ether, di-n-undecyl ether, di-n-dodecyl ether, n-hexyl-n-octyl ether, n-octyl-n-decyl ether, n-decyl-n-undecyl ether, n-undecyl-n-dodecyl ether and n-hexyl-n-undecyl ether, and di-tert-butyl ether, di-iso-pentyl ether, di-3-ethyldecyl ether, tert-butyl-n-octyl ether, iso-pentyl-n-octyl ether and 2-methyl-pentyl-n-octyl ether;

ester oils; ester oils shall be understood to mean the esters of $C_6$ to $C_{30}$ fatty acids having $C_2$ to $C_{30}$ fatty alcohols;

dicarboxylic acid esters such as di-n-butyl adipate, di-(2-ethylhexyl) adipate, di-(2-ethylhexyl) succinate and diisotridecyl acelaate, and diol esters such as ethylene glycol dioleate, ethylene glycol diisotridecanoate, propylene glycol di(2-ethylhexanoate), propylene glycol diisostearate, propylene glycol dipelargonate, butanediol diisostearate, neopentyl glycol dicaprylate, symmetrical, asymmetrical, or cyclic esters of carbonic acid having fatty alcohols, for example described in the unexamined German application DE 197 56 454, glycerol carbonate or dicaprylyl carbonate (Cetiol® CC), trifatty acid esters of saturated and/or unsaturated linear and/or branched fatty acids with glycerol, fatty acid partial glycerides, which shall be understood to mean monoglycerides, diglycerides and the technical mixtures thereof. When technical products are used, small amounts of triglycerides may still be present for manufacturing reasons. The partial glycerides preferably follow the formula (D4-I)

$$\begin{array}{l} CH_2O(CH_2CH_2O)_mR^1 \\ | \\ CH_2O(CH_2CH_2O)_nR^2 \\ | \\ CH_2O(CH_2CH_2O)_qR^3, \end{array} \quad (D4\text{-}I)$$

where $R^1$, $R^2$ and $R^3$ independently of each other denote hydrogen or a linear or branched, saturated and/or unsaturated acyl group having 6 to 22, and preferably 12 to 18, carbon atoms, with the proviso that at least one of these groups denotes an acyl group and at least one of these groups denotes hydrogen. The sum (m+n+q) denotes 0 or numbers from 1 to 100, and preferably 0 or 5 to 25. $R^1$ preferably denotes an acyl group and $R^2$ and $R^3$ denote hydrogen and the sum (m+n+q) is 0. Typical examples are monoglycerides and/or diglycerides based on caproic acid, caprylic acid, 2-ethyl-hexanic acid, caprinic acid, lauric acid, isotridecanic acid, myristic acid, palmitic acid, palmitoleic acid, stearic acid, isostearic acid, oleic acid, elaidic acid, petroselinic acid, linolic acid, linolenic acid, eleostearic acid, arachidic acid, gadoleic acid, behenic acid and erucic acid, and the technical mixtures thereof. Oleic acid monoglycerides are preferably used.

The amounts of natural and synthetic cosmetic oleosomes used in the agents according to the invention is usually 0.1 to 30 wt. %, based on the total application preparation, and preferably 0.1 to 20 wt. %, and more particularly 0.1 to 15 wt. %.

While every one of the aforementioned care substances alone already produces a satisfactory result, all embodiments in which the agent includes multiple care substances, also from various groups, are also covered by the scope of the present invention.

By adding a UV filter, both the agents themselves and the treated fibers can be protected against harmful influences of UV radiation. The UV filters are usually present in amounts of 0.01 to 5 wt. %, based on the total application preparation. Amounts of 0.1 to 2.5 wt. % are preferred.

In one particular embodiment, the agent according to the invention moreover includes one or more direct dyes. This makes it possible to not only temporarily structure, but simultaneously dye the treated keratinic fiber when using the agent. This can be desirable in particular when only temporary coloration, such as with eye-catching fashion colors, is desired, which can be removed from the keratinic fiber again by simple washing.

Direct dyes are usually nitrophenylene diamines, nitroaminophenols, azo dyes, anthraquinones or indophenols. Preferred direct dyes are the compounds known under the international designations or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 11, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52, as well as 1,4-diamino-2-nitrobenzene, 2-amino-4-nitrophenol, 1,4-bis-(β-hydroxyethyl)-amino-2-nitrobenzene, 3-nitro-4-(β-hydroxyethyl)-aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)-amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid and 2-chloro-6-ethylamino-1-hydroxy-4-nitrobenzene. Cationic direct dyes are preferably used. Particularly preferred are (a) cationic triphenylmethane dyes, such as Basic Blue 7, Basic Blue 26, Basic Violet 2 and Basic Violet 14, (b) aromatic systems that are substituted with a quaternary nitrogen group, such as Basic Yellow 57, Basic Red 76, Basic Blue 99, Basic Brown 16 and Basic Brown 17, and (c) direct dyes including a heterocycle which has at least one quaternary nitrogen atom, as they are mentioned in claims 6 to 11 of EP-A2-998 908, for example, which is hereby explicitly referenced.

The dyes that are also known by the designations Basic Yellow 87, Basic Orange 31 and Basic Red 51, are especially particularly preferred cationic direct dyes of group (c). The cationic direct dyes that are sold under the trademark Arianor® are cationic direct dyes that are likewise especially particularly preferred according to the invention.

The agents according to the invention according to this embodiment preferably include the direct dyes in an amount of 0.001 to 20 wt. %, based on the total agent.

It is preferred according to the invention for the agents according to the invention to be free of oxidation dye precursors. Oxidation dye precursors are divided into what are known as developer components and coupler components. Under the influence of oxidizing agents or atmospheric oxygen, the developer components form the actual dyes among each other or by coupling to one or multiple coupler components.

The agents according to the invention can be formulated in all forms that are customary for styling agents, such as in the form of solutions that can be applied as hair tonic or pump spray or aerosol spray to the hair, in the form of creams, emulsions, waxes, gels or also surfactant-containing foaming solutions, or other preparations that are suitable for application to the hair.

A second subject matter of the invention relates to a method for shaping, and more particularly for straightening, keratin-containing fibers, in particular human hair, wherein (i) the fibers are subjected to a heat treatment;

(ii) the heat-treated fibers, subsequently to the heat treatment, are post-treated with a cosmetic agent which includes at least one compound of formula (I) in a cosmetic carrier

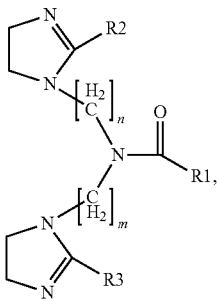

formula (I)

where

R1, R2 and R3 independently of each other denote an aliphatic hydrocarbon group having 6 to 30 carbon atoms; and n and m independently of each other denote integers from 1 to 10, (iii) and the fibers are reshaped after, prior to or during step (i) by way of reshaping aids.

The preferred embodiments of the compounds of formula (I) described within the scope of the first subject matter of the invention and the preferred embodiments of said cosmetic agent described therein are considered, mutatis mutandis, to be preferred.

Reshaping aids within the meaning of the method according to the invention can be hair rollers or curlpapers, for example, in the case of a permanent wave;
a hot air blower, such as a blow dryer or a curling rod;
a hair curler;
or aids for mechanical straightening, such as a comb or a brush, a straightening board or a heatable straightening iron in the case of hair straightening.

At least one heatable straightening iron is especially particularly preferably used as reshaping aid.

Mechanical straightening according to the invention shall be understood to mean a stretching of the curly fiber along the longest spatial extension thereof.

Within the scope of hair straightening, it is preferred to straighten the fibers mechanically, in particular by way of combing or by means of a straightening board.

When the reshaping aids, such as rollers, are attached to the fiber for an extended period within the scope of a waving process, it is expedient to remove these reshaping aids at the latest after step (ii).

In one preferred embodiment of the invention, the keratin-containing fibers are moistened prior to step (i). This can be done by spraying the fibers with a liquid, preferably with water. Prior to step (i), the fibers are preferably shampooed using a conventional shampoo, rinsed, and then dried with a towel. After the towel-drying step, perceptible residual moisture remains in the hair. The fibers can additionally be wetted with a cosmetic agent that promotes the heat treatment, for example facilitates the sliding of heated straightening irons along the fiber during the heat treatment in step (i). Suitable cosmetic agents are described in the document WO-A-2005/115319, for example.

It is preferred according to the invention to dry the fibers prior to the heat treatment of step (i). A dry keratin-containing fiber according to step (ii) of the method according to the invention is present when the remaining water adhering to the hair has evaporated to such an extent that the hair separates individually. In the case of a dry keratin-containing fiber, the moisture content of the fiber is preferably substantially in balance with the moisture in the air, or the fiber absorbs moisture from the surrounding air. Such a dry fiber is preferably achieved by drying the wet fiber with hot air using a blow dryer. The drying prior to step (i) is preferably carried out when a heat treatment takes place in step (i) within the scope of a shaping process, during which the surface of the keratin-containing fibers directly takes place with a temperature-controlled surface of a reshaping aid (such as straightening iron or hair curler) during a shaping step.

In one preferred embodiment, the fibers are subjected to a heat treatment in step (i), while simultaneously reshaping the fiber at a temperature of 50° C. to 350° C. (preferably 80° C. to 280° C., particularly preferably 100° C. to 250° C., more preferably 140° C. to 220° C.). Simultaneous reshaping shall be understood to mean that, during the heat treatment, the fibers are brought into or maintained in a shape, such as by way of mechanical straightening or by fixing the shape by way of rollers or curlpapers.

In one special embodiment, the fibers are subjected to a heat treatment in step (i) within the scope of a hair straightening process, while mechanically straightening the fiber at a temperature of 50° C. to 350° C. (preferably 80° C. to 280° C., particularly preferably 100° C. to 250° C., further preferably 140° C. to 220° C.). The heat treatment can be carried out using hot air. In this case, the fiber is heated during combing at precisely the location at which the mechanical straightening takes place. It is moreover particularly preferred for the heat treatment to be carried out in the manner of a straightening process by way of what is known as a straightening iron having appropriately temperature-controlled plates, in particular metal or ceramic plates, by pressing the plate onto the fiber that is to be straightened and then moving the plate, which is pressed against the fiber, along the fiber. The plates can optionally be coated with heat-resistant materials. The keratin-containing fiber to be straightened is particularly preferably pressed between two appropriately temperature-controlled plates, and both plates are moved simultaneously along the longest spatial extension of the fiber. It is preferred for the two plates to be connected to each other, so that both plates can be moved evenly along the fiber. If the heat treatment is carried out on alive hair, the fiber is attached at one end (root of the hair). In this case, the plates are preferably moved evenly along the entire fiber away from the root of the hair. This movement mechanically straightens the fiber. A corresponding device for heat treatment is the device "Ceramic Flat-Master" (sold by: Efalock, Germany) or Schwarzkopf Professional: model no. IP30A, for example.

In one further embodiment, the fibers are subjected to a heat treatment in step (i) within the scope of a waving process, while mechanically curling the fiber at a temperature of 50° C. to 350° C. (preferably 80° C. to 280° C., particularly preferably 100° C. to 250° C., more preferably 140° C. to 220° C.). The heat treatment can be carried out using a hot air blower. In this case, the fiber is either wrapped around an appropriate hot air curling rod and heated at precisely the location at which the curling takes place or the fibers are wrapped onto hair rollers as reshaping aid and heated using a blow dryer. A further option of heat-assisted waving is carried out by wrapping the fibers around a rod having an appropriately heated surface, without the use of a hot air blower, and heating at precisely the location at which the curling takes place. A corresponding device for heat treatment is the device from Schwarzkopf Professional, model no.: CPL type F37, for example.

A particularly preferred embodiment of the present invention is defined by the following items:

1. Use of at least one compound of formula (I)

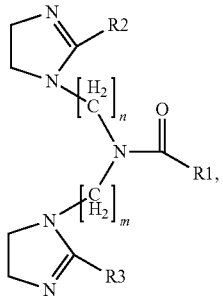

formula (I)

where

R1, R2 and R3 independently of each other denote an aliphatic hydrocarbon group having 6 to 30 carbon atoms; and n and m independently of each other denote integers from 1 to 10, for restructuring keratin-containing fibers which were exposed to heat having a temperature of 80° C. to 350° C. (preferably 80° C. to 280° C., particularly preferably 100° C. to 250° C., and more preferably 140° C. to 220° C.).

2. Use according to item 1, characterized in that the heat source is a straightening iron or a hair curler.

3. Use according to either item 1 or 2, characterized in that said aliphatic hydrocarbon group of the groups R1, R2 and R3 denotes a C6 to C30 alkyl group or a C6 to C30 alkenyl group (particularly preferably a C8 to C24 alkyl group or a C8 to C24 alkenyl group, especially particularly preferably a C10 to C20 alkyl group or a C10 to C20 alkenyl group, and most preferably a C12 to C18 alkyl group or a C12 to C18 alkenyl group).

4. Use according to any one of items 1 to 3, characterized in that at least the groups R2 and R3 of formula (I) are identical.

5. Use according to any one of items 1 to 4, characterized in that the groups R1 and R2 and R3 of formula (I) are identical.

6. Use according to any one of items 1 to 5, characterized in that according to formula (I), n=m.

7. Use according to any one of items 1 to 6, characterized in that n and m of formula (I) denote integers from 2 to 6, and most preferably denote 2, 3 and/or 4.

8. Method for shaping, more particularly for straightening, keratin-containing fibers, in particular human hair, wherein:

(i) the fibers are subjected to a heat treatment;

(ii) the heat-treated fibers, subsequently to the heat treatment, are post-treated with a cosmetic agent which includes at least one compound of formula (I) in a cosmetic carrier

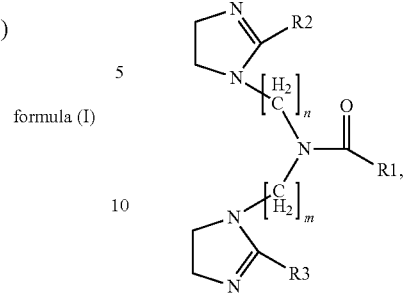

formula (I)

where

R1, R2 and R3 independently of each other denote an aliphatic hydrocarbon group having 6 to 30 carbon atoms; and n and m independently of each other denote integers from 1 to 10, (iii) and the fibers are reshaped after, prior to or during step (i) by way of reshaping aids.

9. Method according to item 8, characterized in that the fibers are subjected to a heat treatment in step (i), while simultaneously reshaping the fiber at a temperature of 50° C. to 350° C. (preferably 80° C. to 280° C., particularly preferably 100° C. to 250° C., more preferably 140° C. to 220° C.).

10. Method according to either item 8 or 9, characterized in that at least one heatable straightening iron is used as reshaping aid.

11. Method according to any one of items 8 to 10, characterized in that the compound of formula (I) is defined as in one of items 3 to 8.

12. Method according to any one of items 8 to 11, characterized in that the compounds of above formula (I) are present in an amount of 0.01 to 15.0 wt. %, particularly preferably of 0.1 to 10.0 wt. %, especially particularly preferably of 0.1 to 7.5 wt. %, and most preferably of 0.3 to 5.0 wt. %, in each case based on the weight of the ready-to-use agent.

EXAMPLES

All quantities are listed in wt. % based on the total weight of the agent, unless not otherwise indicated.

1.0 Example Formulation

The following cosmetic agent according to the invention was produced by mixing the components.

TABLE 1

| Raw material | Amount |
| --- | --- |
| Luviskol VA 64 W[1] | 5.00 |
| Gluadin WQ[2] | 1.00 |
| Keradyn HH-LQ-(RB)[3] | 1.00 |
| Sodium benzoate | 0.10 |
| Cetyltrimethylammonium chloride | 0.50 |
| Ortho-phosphoric acid | 0.024 |
| Hydrolyzed silk protein | 0.50 |
| PEG-40 hydrogenated castor oil | 2.50 |
| Ethanol | 5.00 |
| Water (distilled) | up to 100 |

[1] Copolymer of vinylpyrrolidone and vinylacetate (60:40) (48-52% active substance in water, INCI designation: VP/VA Copolymer) (BASF)
[2] Whey protein hydrolysate (approx. 31-35% dry substance; INCI designation: Aqua (Water), Laurdimonium Hydroxypropyl Hydrolyzed Wheat Protein, Ethylparaben, Methylparaben) (BASF SE)
[3] Bis-Ethyl(isostearylimidazoline) Isostearamide (Croda)

2.0 Proof of Efficacy:

The above composition was used for the proof of efficacy.

2.1 Test Method HP-DSC (High Pressure Differential Scanning Calorimetry)

Thermoanalytical examinations are particularly suitable for characterizing two-phase systems, which also include human hair as fiber keratins with their crystalline α-helix component and amorphous matrix component. This allows not only glass transitions and aging behavior of the amorphous matrix to be examined, but the melting behavior of the crystalline, helical phase also provides important information. Thermoanalytical examinations were described for the first time in 1899; the first differential thermal analyses (DTA) of protein fibers were carried out toward the end of the fifties. In the years thereafter, various thermoanalytical measuring methods, such as DTA, HP-DTA (high pressure DTA) and DSC (differential scanning calorimetry), were applied to keratin fibers to examine, for example, the phenomenon of supercontraction, α-β phase transitions of the helices, or denaturing processes. The HP-DSC method was used to study keratin fibers; the method eliminates the problems associated with pyrolytic effects as they occur in conventional DSC, and the problems with data acquisition and interpretation as found with DTA. DSC measurements are carried out on keratins which are encapsulated with water in commercially available, pressure-resistant measuring capsules. In the keratin-water system, a high water vapor pressure develops in the encapsulated steel crucibles on heating of above 100° C., from which the HP-DSC analysis derives. The crucial difference between HP-DSC thermograms of human hair and regular DSC thermograms is that the endothermic peaks, which reflect the transformation point and transformation enthalpy, are shifted here by approximately 90° C. to lower temperatures. This is due to the fact that water, after diffusion into the hair fiber, lowers protein stability by weakening and breaking up hydrogen bonds and salt bonds, thereby reducing the "cementing temperature" of the keratins. If only hydrogen bonds and salt bonds are dissolved by the supercontracting agent, such as water, the thermal effect is reversible (supercontraction). However, the process becomes irreversible as soon as covalent bonds, such as disulfide bonds, are also broken up. This takes place when human hair fibers are heated in pressure-resistant capsules with water to above 150° C. The irreversible transformation, interpreted as a transition of the α-helical regions in the proteins into a disordered state, results in endothermic peaks, wherein the position of the peaks reflects the transformation or denaturing point and the peak area reflects the transformation or denaturing enthalpy.

Using differential scanning calorimetry (DSC), it is thus possible to detect structural and chemical states and changes in fiber keratins, and in particular in human hair. Under precisely defined test conditions, the processes detectable by calorimetry in human hair can be recorded in the form of thermograms, and the peak positions, structures and areas thereof can be used as an indicator of the influence that changes in inner and/or outer parameters, for example, by cosmetic treatment of the hair, have on order/disorder transitions. This means that information about the strength or damage of the human hair fiber can be derived from the endothermic peaks recorded in the thermogram of human hairs based on the peak position (transformation point) and peak area (transformation enthalpy).

Detailed examinations regarding the influence of the cystine content on the denaturing of the α helices in keratins have shown, for example, that the denaturing temperature (transition temperature) of the keratin rises linearly with the cystine content. The increased stability of the matrix region, resulting from the higher degree of crosslinking of the increased share of disulfide bonds in the matrix, makes the transformation of the helices embedded in this matrix more difficult, thus resulting in an increase in the denaturing temperature. Conversely, a denaturing temperature reduction, and especially a denaturing enthalpy reduction, can generally be observed in human hair treated by permanent waving or bleaching or dyeing (H. Deutz, doctoral thesis, RWTH Aachen 1993).

2.2 Procedure 2.2.1 Variant of the Method "Use of the Compound According to Formula (I) when Straightening Hair"

Human hair strands (Kerling International (Backnang, Germany) "European natural hair 7/0") were treated with 0.7 g of one of the test compositions listed in Table 1 per 1.8 g of strand and dried by exposure to air without a rinsing step.

A straightening iron (brand: Schwarzkopf Professional; model no. IP30A) was heated at the highest setting (210° C.) for at least 10 minutes. The temperature between the heating plates, measured with a contact thermometer (brand: Qtemp 300), was 180° C. after 10 minutes.

The dried hair strand was then straightened using the preheated straightening iron. The following movement of the straightening iron along the hair fiber was ensured: 4 times brief (1 second each per hair strand), 2 times long (5 seconds per hair strand).

The temperatures that were reached fluctuated between 146 and 181° C.

The hair strand was cooled to room temperature by exposure to air, rinsed for approximately 1 minute with water (water temperature approx. 35 to 39° C.), excess water was removed using fingers, and the strand was patted dry with a towel, hung up, and allowed to rest and dry.

This treatment was repeated 40 times for each strand.

2.2.2 Variant of the Method "Use of the Compound of Formula (I) as a Post-Treatment Agent after Straightening"

Human hair strands (Kerling International (Backnang, Germany) "European natural hair 7/0") were used. A straightening iron (brand: Schwarzkopf Professional; model no. IP30A) was heated at the highest setting (210° C.) for at least 10 minutes. The temperature between the heating plates, measured with a contact thermometer (brand: Qtemp 300), was 180° C. after 10 minutes.

The hair strand was then straightened using the preheated straightening iron. The following movement of the straightening iron along the hair fiber was ensured: 4 times brief (1 second each per hair strand), 2 times long (5 seconds per hair strand). The temperatures that were reached fluctuated between 146 and 181° C.

The hair strand was cooled to room temperature by exposure to air. Thereafter the above agent was applied to the fiber and left on the fiber over night.

The strand was then rinsed for approx. 1 minute with water (water temperature approx. 35 to 39° C.), excess water was removed using fingers, and the strand was patted dry with a towel, hung up, and allowed to rest and dry.

This treatment was repeated 40 times for each strand.

2.3 Thermoanalytical Examination

By way of thermoanalytical examinations (DSC device: Perkin Elmer DSC 7, 60 μl stainless steel crucible with O-ring (24 atm)), tests were conducted for a structural stabilization by the test composition after repeated application of heat, i.e. after the respective processes from 2.2.1 and 2.2.2 were concluded. Each strand was divided into portions of approximately 1 mm each. 12 of these aliquots of the same strand were filled into a DSC measuring crucible and placed in 50 μl double distilled water. The measuring crucibles were closed, and the sample was measured at a temperature interval of 100° C. to 170° C. (heating rate: 10 kelvin per minute). The untreated starting hair likewise underwent HP-DSC measurement.

5 strands were tested for each method variant. The keratin melting points calculated by way of arithmetic means from the individual measurements are listed in Table 2.

TABLE 2

Heat protection of the structure by the active agent combination according to the invention

| Method | Keratin melting point [° C.] |
| --- | --- |
| During heat application | 131.6 |
| Post-treatment | 136.3 |
| Untreated starting hair | 155.2 |

The keratin melting point of the strands post-treated with the compounds of formula (I) is significantly higher than that of the strands to which compounds of formula (I) were applied during the application of heat. The post-treatment thus effectively protects the hair structure from the action of heat.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for shaping, keratin-containing fibers, wherein
    (i) the fibers are subjected to a heat treatment;
    (ii) the heat-treated fibers, subsequently to the heat treatment, are post-treated with a cosmetic agent which includes at least one compound of formula (I) in a cosmetic carrier

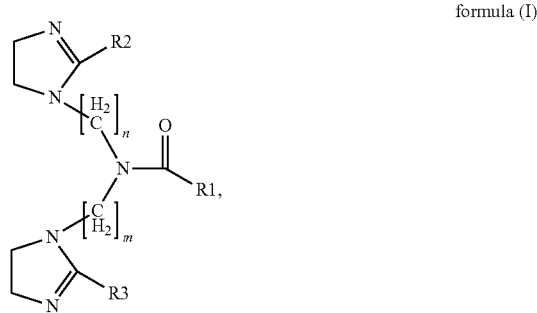

formula (I)

where—R1, R2 and R3 independently of each other denote an aliphatic hydrocarbon group having 6 to 30 carbon atoms; and —n and m independently of each other denote integers from 1 to 10,
    (iii) and the fibers are reshaped after, prior to or during step (i) by way of reshaping aids.

2. The method according to claim 1, wherein the shaping of the keratin-containing fibers is straightening of the keratin-containing fibers.

3. The method according to claim 1, wherein the fibers are subjected to a heat treatment in step (i), while simultaneously styling the fiber at a temperature of 50° C. to 350° C.

4. The method according to claim 1, wherein the fibers are subjected to a heat treatment in step (i), while simultaneously styling the fiber at a temperature of 80° C. to 280° C.

5. The method according to claim 1, wherein the fibers are subjected to a heat treatment in step (i), while simultaneously styling the fiber at a temperature of 100° C. to 250° C.

6. The method according to claim 1, wherein at least one heatable straightening iron is used as a reshaping aid.

7. The method according to claim 1, wherein the aliphatic hydrocarbon group of the groups R1, R2 and R3 denotes a C6 to C30 alkyl group or a C6 to C30 alkenyl group.

8. The method according to claim 1, wherein the aliphatic hydrocarbon group of the groups R1, R2, and R3 denotes a C8 to C24 alkyl group or a C8 to C24 alkenyl group.

9. The method according to claim 1, wherein the aliphatic hydrocarbon group of the groups R1, R2, and R3 denotes a C10 to C20 alkyl group or a C10 to C20 alkenyl group.

10. The method according to claim 1, wherein the aliphatic hydrocarbon group of the groups R1, R2, and R3 denotes a C12 to C18 alkyl group or a C12 to C18 alkenyl group.

11. The method according to claim 1, wherein the groups R2 and R3 of formula (I) are identical.

12. The method according to claim 1, wherein the groups R1 and R2 and R3 of formula (I) are identical.

13. The method according to claim 1, wherein the compounds of above formula (I) are included in an amount of 0.01 to 15.0 wt. % based on the weight of the ready-to-use agent.

14. The method according to claim 1, wherein the compounds of above formula (I) are included in an amount of 0.1 to 10.0 wt. % based on the weight of the ready-to-use agent.

15. The method according to claim 1, wherein the compounds of above formula (I) are included in an amount of 0.1 wt. % to 7.5 wt. % based on the weight of the ready-to-use agent.

16. The method according to claim 1, wherein n=m in formula (I).

17. The method according to claim 1, wherein n and m of formula (I) denote integers from 2 to 6.

18. The method according to claim 1, wherein n and m of formula (I) denote the integers 2, 3 or 4.

* * * * *